(12) United States Patent
Krishnan et al.

(10) Patent No.: US 9,752,159 B2
(45) Date of Patent: Sep. 5, 2017

(54) STABLE EXPRESSION SYSTEM FOR EUKARYOTIC CELLS

(71) Applicant: BioGenomics Limited, Thane West (IN)

(72) Inventors: Archana Rajesh Krishnan, Thane (IN); Sanjay Madhukar Sonar, Thane (IN); Damodar Krishnabahadur Thappa, Mumbai (IN)

(73) Assignee: BIOGENOMICS LIMITED, Thane West, MH (IN)

( * ) Notice: Subject to any disclaimer, the term of this patent is extended or adjusted under 35 U.S.C. 154(b) by 127 days.

(21) Appl. No.: 14/388,936

(22) PCT Filed: Apr. 1, 2013

(86) PCT No.: PCT/IN2013/000216
§ 371 (c)(1),
(2) Date: Sep. 29, 2014

(87) PCT Pub. No.: WO2013/175491
PCT Pub. Date: Nov. 28, 2013

(65) Prior Publication Data
US 2015/0118754 A1    Apr. 30, 2015

(30) Foreign Application Priority Data
Mar. 30, 2012   (IN) ............................ 991/MUM/2012

(51) Int. Cl.
*C12N 15/85*    (2006.01)

(52) U.S. Cl.
CPC .......... *C12N 15/85* (2013.01); *C12N 2830/46* (2013.01); *C12N 2830/50* (2013.01); *C12N 2840/203* (2013.01)

(58) Field of Classification Search
None
See application file for complete search history.

(56) References Cited

U.S. PATENT DOCUMENTS 7,935,808 B2 *   5/2011   Gion ...................... C07K 16/00
                                                                            424/93.2

OTHER PUBLICATIONS

Baldi, et al. (2006) "Recombinant protein production by large-scale transient gene expression in mammalian cells: state of the art and future perspectives", Biotechnology Letters, 29(5): 677-84.*
Trill, et al. (2001) "Chapter 16: Eukaryotic Expression", Molecular Biology Problem Solver: A Laboratory Guide, Published by Wiley-Liss, Inc., New York, NY, 491-542.*
Lee, et al. (2009) "Overexpression of heat shock proteins (HSPs) in CHO cells for extended culture viability and improved recombinant protein production", Journal of Biotechnology, 143(1): 34-43.*
Gurtu, et al. (1996) "IRES Bicistronic Expression Vectors for Efficient Creation of Stable Mammalian Cell Lines", Biochemical and Biophysical Research Communications, 229(1): 295-98.*
Girod, et al. (2005) "Use of the chicken lysozyme 5' matrix attachment region to generate high producer CHO cell lines", Biotechnology and Bioengineering, 91(1): 1-11.*
Lin, et al. (2010) "Generating Stable Chinese Hamster Ovary Cell Clones to Produce a Truncated SARS-CoV Spike Protein for Vaccine Development" Biotechnology Progress, 26(6): 1733-40.*
Wang, et al. (2010) "Positional effects of the matrix attachment region on transgene expression in stably transfected CHO cells", Cell Biology International, 34: 141-45.*

* cited by examiner

*Primary Examiner* — Robert M Kelly
(74) *Attorney, Agent, or Firm* — Merchant & Gould P.C.

(57) ABSTRACT

The present invention related to a polynucleotide sequence and an expression vector comprising at least one gene encoding a stress resistance protein, at least one gene encoding a selection marker, at least one gene encoding an expression protein, at least one matrix attachment region and a transcription terminator, all of which are operably connected to each other. The present invention further relates to a host cell comprising the expression vector. The present invention also relates a method of producing a cell line.

10 Claims, 3 Drawing Sheets

STABLE EXPRESSION SYSTEM FOR EUKARYOTIC CELLS

CROSS REFERENCE TO RELATED APPLICATION

This application is a National Stage Application of International Application No. PCT/IN2013/000216 filed on Apr. 1, 2013, which claims benefit of Indian Application No. 991/MUM/2012 filed on Mar. 30, 2012, and which applications are incorporated herein by reference in their entireties. To the extent appropriate, a claim of priority is made to each of the disclosed application.

This application contains sequence listing that has been submitted as an ASCII file named RIPLLC036.003SEQ_ST25, the date of creation Jan. 9, 2015, and the size of the ASCII text file in bytes is 13 kb.

FIELD OF THE INVENTION

The present invention relates to a polynucleotide sequence and an expression vector for a eukaryotic cell to express a protein of interest. Furthermore, the present invention relates to an expression vector that prolongs life of cell line.

BACKGROUND

Recombinant technology has been used to clone, express and purify several proteins of therapeutic or other economic value. Use of Eukaryotic host cells to express large quantity of recombinant proteins in large amounts has become increasingly important because of the ability of Eukaryotic cells to express the protein of interest in desired conformation. Method to improve protein expression often includes increasing gene dosage or copies, or by adding genetic elements that prolong life of cells. Various factors affect the ability of the expression vector to express the protein during fermentation. These include selection marker gene used for selection of vector containing cells from other cells, Orientation of the genes coding for product of interest, strength of the promoter linked to the gene for protein of the interest, the sequence of the 5' untranslated and the translation initiation region, the efficiency of the 3' untranslated region to polyadenylate and terminate transcription, the insertion site of the randomly integrated recombinant gene in the host chromosome, and the number of integrated copies of the gene that is being expressed. In spite of the plethora of available vectors, production of robust cell lines producing the polypeptide/protein at high concentration in a consistent manner is still challenging. Several other factors can influence the yield for expression of recombinant protein in mammalian cells, some of them are protein to be expressed, Media components, Host cell lines used, etc.

Other problem associated with industrial production of recombinant proteins using eukaryotic cells is related to stress conditions incurred by cells during the late stages of fermentation. During the late phases of the fermentation the number of cells are more as compared to early phases of fermentation. Hence, the protein of interest is produced at much faster rate. During the late phase of the fermentation, the cells are exposed to stress conditions such as high temperature, high osmotic pressure, metabolic inhibition, presence of heavy metals, viral infection, etc. These factors negatively affect the fermentation process and expression of the protein of interest by increasing the rate of cell death. The increase in cell death results in decrease in time of the fermentation cycles per batch. This result in decrease in overall yield of the protein produced per batch. This leads to increases in duration of the fermentation cycle to improve the overall yield of protein of interest and thus increasing the cost of production.

The patent application U.S. Pat. No. 7,935,808 discloses REVE sequences which may comprise one or more matrix attachment region (MAR) sequences. MAR sequences may occur in clusters within a rEVE sequence, including in clusters at the 5' and/or 3' terminal regions of a rEVE sequence. It further discloses Dihyrofolate reductase for higher survivability and/or higher growth rate. The patent discloses use of Heat shock protein (HSP) with other elements like MAR, gene of interest to achieve stable cell. However, the incorporation of three genes i.e. HSP gene, MAR sequence and Gene for protein, into its genome at a stable location is not disclosed.

Despite significant progress in improving the yield from these cells, the process to the selection, identification, and maintenance of high-producing cell lines remains cumbersome, time consuming, and often of uncertain outcome. Thus, there is a need in the art to design improved expression vectors useful for protein expression in mammalian cells which can overcome the deficiencies of the known methods and thus improve the expression of the vectors to yield highly stable and viable cell lines. In the present invention, the vectors so designed will provide an efficient generation of stable cell lines expressing the product of interest at desired levels. The vector generates a high expression stable cells lines with higher viability and stability and yet reduces the total time of fermentation by reducing the number of fermentation cycles and overcomes the drawbacks presented by the prior art.

SUMMARY OF THE INVENTION

Surprisingly, the inventors have developed a polynucleotide sequence for a eukaryotic cell which for instance, generates high expression stable cell lines with higher viability and stability. The polynucleotide sequence comprises:
at least one promoter;
at least one gene encoding a stress resistance protein;
at least one gene encoding a selection marker;
at least one gene encoding an expression protein; and,
a transcription terminator, all of which are operably connected to each other Also, surprisingly the inventors have discovered an expression vector for a eukaryotic cell comprising:
at least one promoter;
at least one gene encoding a stress resistance protein;
at least one gene encoding a selection marker;
at least one gene encoding an expression protein; and,
a transcription terminator, all of which are operably connected to each other.

Furthermore, the expression vector for a eukaryotic cell demonstrates excellent protein expression, high stability and viability and can be effectively used for the production of protein of interest.

The present invention relates to an expression vector comprising polynucleotide sequence of SEQ ID. NO: 1.

The present invention relates to a host cell comprising the expression vector. Further, surprisingly the inventors of the application have discovered a method of producing a stable and viable cell lines comprising, for the expression of a gene of interest in a host cell, the method comprises transfecting a host cell with the expression vector and, culturing the transfected host cell.

Quite advantageously, the method of producing cell line comprising the expression vector can be used efficiently for production of protein of interest with high expression, stability and longer viability of the strain containing the expression vector and it still further expedites the production of protein of interest by reducing the number of fermentation cycles

BRIEF DESCRIPTION OF THE DRAWINGS

For a more complete understanding of the invention, reference should now be made to the embodiment illustrated in greater detail in the accompanying drawing and described below by way of examples of the invention.

DETAILED DESCRIPTION OF THE INVENTION

Figure 1:
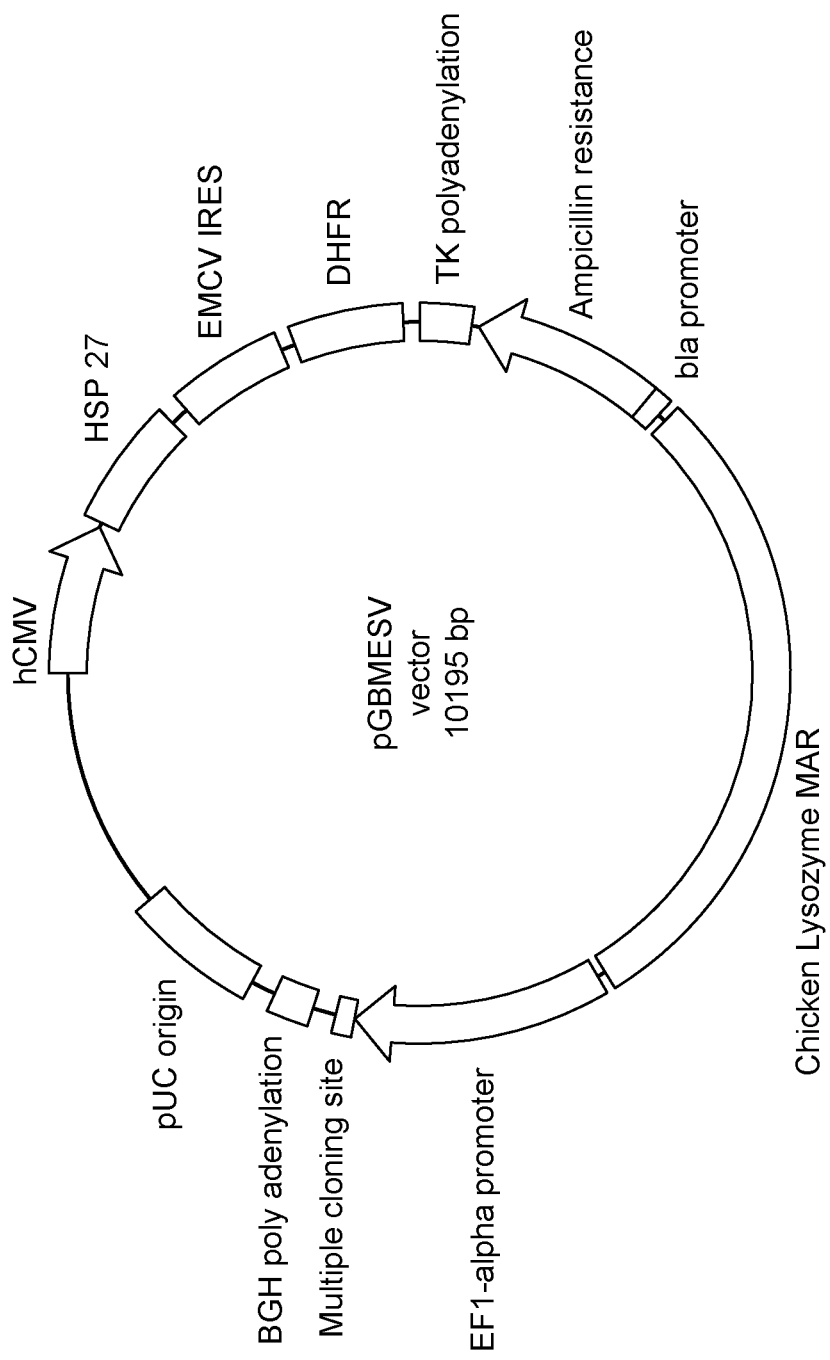
FIG. 1: illustrates the fragments of the expression vector pBGMESV in accordance with the embodiment of the invention.

As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. Further, the terms and phrases used herein are not intended to be limiting but rather to provide an understandable description of the invention.

The terms "a" or "an", as used herein, are defined as one or more than one. The term "plurality", as used herein, is defined as two or more than two. The term "another", as used herein, is defined as at least a second or more. The terms "including" and/or "having", as used herein, are defined as comprising (i.e., open language).

The present invention provides an expression vector for a eukaryotic cell that demonstrates excellent protein expression, high stability and viability and can be effectively used for the production of protein of interest. Such vectors are referred to herein as plasmid BioGenomics Mammaliam Expression Super Vector (pBGMESV).

As described herein, the abbreviation MTX refers to Methotrexate. As described herein, the abbreviation "DHFR" refers to Dihydrofolate reductase. As described herein, the abbreviation "CHO" refers to chicken lysozyme enzyme. As described herein, the abbreviation "HRP-Conjugated antibody" refers to Horseradish Peroxidase-Conjugated antibody. As described herein, the abbreviation "hCMV promoter" refers to Human cytomegalovirus promoter. As described herein, the abbreviation "pBUD-EPO" refers to pBUD-Erythropoietin (INVITROGEN, 4595 bp), As described herein, the abbreviation "HSP" refers to Heat shock proteins. As described herein, the abbreviation "MAR" refers to Matrix attachment region. As described herein, the abbreviation "IRES" refers to internal ribosome entry site Vector Deposition: The vector pBGMESV is deposited for the patent purposes under Budapest Treaty at the MTCC (Microbial Type of Culture Collection) Chandigarh, India. The deposit was made on 20 Jan., 2011 and accorded deposit number for the same. The deposit number for vector pBGMESV is MTCC 5682. The sequence was characterised using DNA Sequencer.

The invention relates to, a polynucleotide sequence for a eukaryotic cell which comprises:
at least one promoter;
at least one gene encoding a stress resistance protein;
at least one gene encoding a selection marker;
at least one gene encoding an expression protein; and,
a transcription terminator, all of which are operably connected to each other According to an embodiment, the polynucleotide comprises an internal ribosome entry site (IRES) linked to the gene encoding the selection marker. According to an embodiment, the polynucleotide sequence wherein the internal ribosome entry site (IRES) can be Picornavirus IRES, Aphthovirus IRES, Hepatitis A IRES, Hepatitis C IRES, Pestivirus IRES, Cripavirus IRES, Kaposi's sarcoma-associated herpes virus IRES or combination thereof.

Other IRES sequences of the polynucleotide sequence known to those skilled in the art can also be utilized for expression of the gene for selection marker in accordance with the present invention. According to an embodiment, the polynucleotide sequence wherein the polynucleotide comprises at least one matrix attachment region.

According to an embodiment, MAR of the polynucleotide sequence can be Humans, Xenopus, mouse, or any other plant and animal sources or fragments thereof In a preferred embodiment, the MAR of the polynucleotide sequence is chicken lysozyme MAR element.

According to another embodiment, MAR of the polynucleotide sequences are identified, isolated, and cloned using a variety of techniques well known to those of ordinary skilled in the art. According to an embodiment, the stress resistance protein of the polynucleotide sequence can be one of HSP 70, HSP 90, HSP 27, or a combination thereof. In a preferred embodiment, the stress resistance protein of the polynucleotide sequence is HSP27.

According to an embodiment, the selection marker of the polynucleotide sequence is optionally linked to the internal ribosome entry site. According to an embodiment, the selection marker of the polynucleotide sequence can be a glutamine synthatase, dihydrofolate reductase, antibiotic resistance gene, auxotrophic marker, or combination thereof.

In a preferred embodiment, the selection marker of the polynucleotide sequence is dihydrofolate reductase. According to another embodiment, the promoter of the polynucleotide sequence can be a PEF 1 alpha promoter, a hCMV promoter, or a HSP promoter. According to yet another embodiment, the transcription terminator of the polynucleotide sequence is bovine growth hormone polyadenylation signal.

According to another embodiment, the gene encoding an expression protein of the polynucleotide sequence encodes insulin and insulin analogues, trypsin, carboxypeptidase, DNA ligase, interferons and their conjugates, filgrastim and its conjugates, polymerases, bevacizumab, trastuzumab, infliximab, rituximab, adalimumab, erythropoietin, etanercept, ranibizumab, transferrins, kinases, growth hormones, or albumin or any other recombinant protein of therapeutic or non-therapeutic significance. According to an embodiment, enhancer elements of the polynucleotide sequence are optionally included in one or more of the vectors of the invention.

According to an embodiment, an expression vector for a eukaryotic cell comprising:
at least one promoter;
at least one gene encoding a stress resistance protein;
at least one gene encoding a selection marker;
at least one gene encoding an expression protein; and,
a transcription terminator, all of which are operably connected to each other.

According to an embodiment, an expression vector for an animal cells comprising:
at least one promoter;
at least one gene encoding a stress resistance protein;
at least one gene encoding a selection marker;
at least one gene encoding an expression protein; and,
a transcription terminator, all of which are operably connected to each other.

According to an embodiment, the expression vector comprises an internal ribosome entry site (IRES) linked to the gene encoding the selection marker. Other IRES sequences of the expression vector known to those skilled in the art can also be utilized for expression of the gene for selection marker in accordance with the present invention. According to an embodiment, the expression vector comprises the Internal ribosome entry site (IRES) can be Picornavirus IRES, Aphthovirus IRES, Hepatitis A IRES, Hepatitis C IRES, Pestivirus IRES, Cripavirus IRES, Kaposi's sarcoma-associated herpes virus IRES, or combination thereof.

According to an embodiment, the expression vector comprises MAR. According to an embodiment, MAR of the expression vector can be humans, Xenopus, mouse, or any other plant and animal sources or fragments thereof. In a preferred embodiment, the MAR of the expression vector can be chicken lysozyme MAR element. According to another embodiment, MAR of the expression vectors are identified, isolated, and cloned using a variety of techniques well known to those of ordinary skilled in the art.

According to an embodiment, the stress resistance protein of the expression vector can be HSP 70, HSP 90, HSP 27, or combination thereof. In a preferred embodiment, the stress resistance protein of the expression vector is HSP27. According to an embodiment, the selection marker of the expression vector is linked to the internal ribosome entry site.

According to an embodiment, the selection marker of the expression vector is can be glutamine synthatase, dihydrofolate reductase, antibiotic resistance gene, auxotrophic marker or combination thereof. In a preferred embodiment, the selection marker of the expression vector is dihydrofolate reductase. According to another embodiment, the promoter of the expression vector can be a PEF 1 alpha promoter, hCMV promoter, or an HSP promoter.

According to yet another embodiment, the transcription terminator of the expression vector is bovine growth hormone polyadenylation signal. According to another embodiment, the gene encoding an expression protein of the expression vector encodes insulin and insulin analogues, trypsin, carboxypeptidase, DNA ligase, interferons and their cojugates, filgrastim and its conjugates, polymerases, bevacizumab, trastuzumab, infliximab, rituximab, adalimumab, erythropoietin, etanercept, ranibizumab, transferrins, kinases, growth hormones, or albumin. According to an embodiment, an expression vector is comprising a polynucleotide sequence comprising of the nucleotide base sequence of SEQ ID NO: 1. The polynucleotide sequence has 9516 base pairs (FIG. 1)

According to an embodiment, the expression vector pBGMESV comprises:
at least one promoter;
at least one gene encoding a stress resistance protein;
at least one gene encoding a selection marker;
at least one gene encoding an expression protein; and,
a transcription terminator, all of which are operably connected to each other.

According to an embodiment, the expression vector pBGMESV further comprises an internal ribosome entry site (IRES) linked to the gene encoding the selection marker. According to an embodiment, the expression vector pBGMESV, comprises at least one matrix attachment region. According to an embodiment, enhancer elements of the expression vector are optionally included in one or more of the vectors of the present invention.

Figure 2:
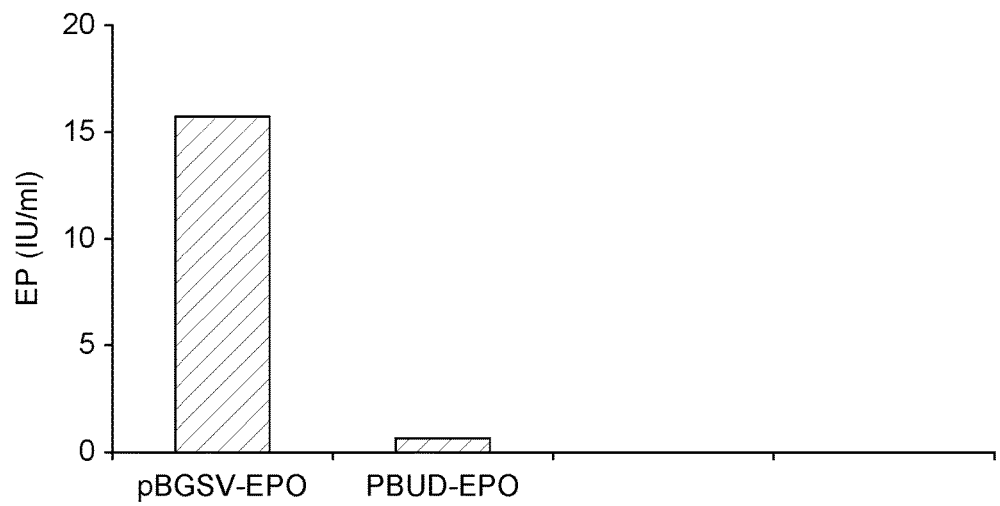
FIG. 2: illustrates the yield achieved for transient transfection of CHO DHFR⁻ cells with pBGMESV-EPO in accordance with an embodiment of the invention and pBUD-EPO expression vectors.

According to an embodiment, a method of transforming one or more eukaryotic cells comprising at least one gene encoding a matrix attachment region, at least one gene encoding a stress resistance protein, at least one gene encoding an expression protein. According to another embodiment, the genes can be present in a plurality of vectors. According to an embodiment, after the transformation of cell cultures, higher titre clones, are selected by known methods under standard conditions. According to an embodiment, FIG. 1 illustrates the fragments of the expression vector pBGMESV. According to an embodiment, FIG. 2 illustrates the yield achieved for transient transfection of CHO DHFR⁻ cells with pBGMESV-EPO and pBUD-EPO expression vectors.

Figure 3:
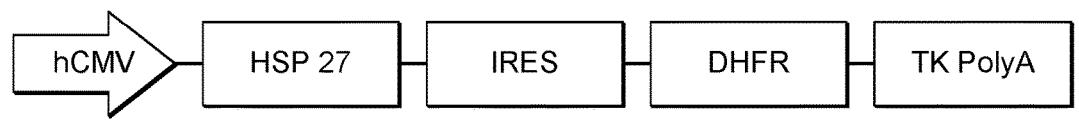
FIG. 3: illustrates hCMV promoter linked to HSP 27 gene which is connected to IRES linked DHFR gene having thymidine kinase Polyadenylation sequence at 5' end in accordance with the embodiment of the invention.
Figure 4A:
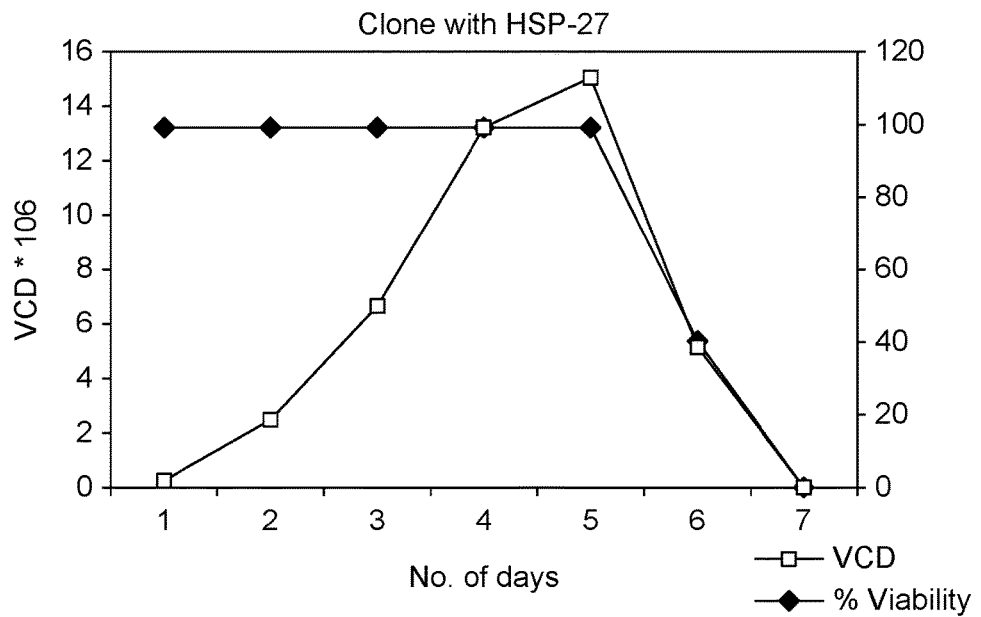
FIG. 4a and FIG. 4b: illustrates comparison between the cell count and cell viability of the mammalian cells in pBGMESV vector and in a vector without HSP and MAR
Figure 4B:
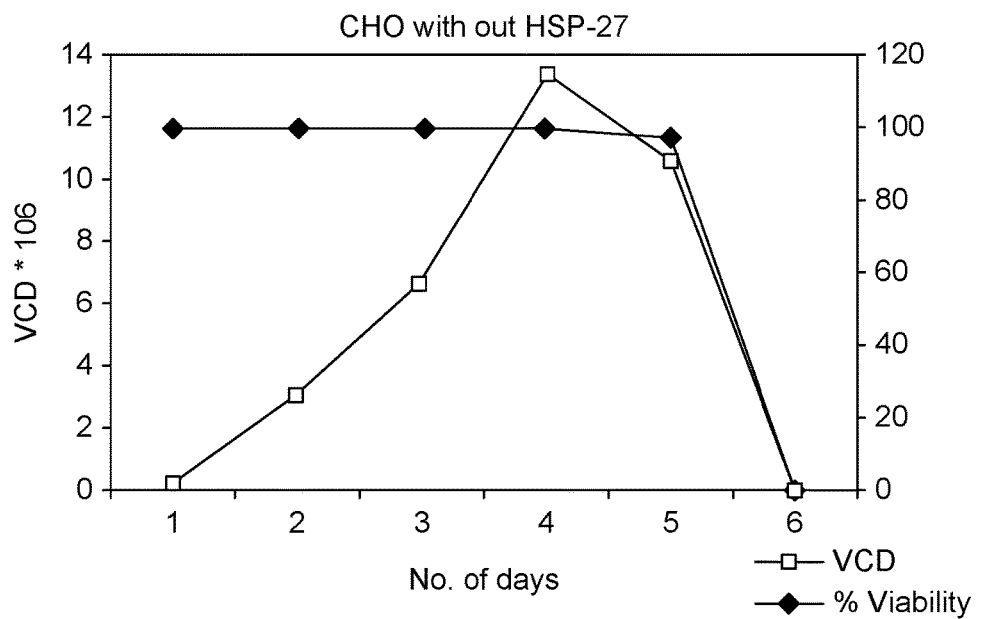

According to an embodiment, FIG. 3 illustrates hCMV promoter linked to HSP 27 gene which is connected to IRES linked DHFR gene having thymidine kinase Polyadenylation sequence at 5' end. According to an embodiment, FIGS. 4a and 4b illustrates comparison of the cell count and cell viability of the mammalian cells in pBGMESV vector and in a vector without HSP and MAR.

According to another embodiment, a host cell comprises of the polynucleotide sequence of SEQ ID NO: 1. According to another embodiment, a host cell comprises the expression vector. According to an embodiment, the eukaryotic cell type can be. stem cells, embryonic stem cells, COS, BHK21, NIH3T3, HeLa, C2C12, CHO-K1, CHO DG44, DXB11, CHO-S, NS0, BHK, Vero, Per C6, HEK293 cells, cancer cells and primary differentiated or undifferentiated cells. Other suitable host cells known to those skilled in the art can also be used in accordance with the present invention. According to an embodiment, a method of producing stable and viable cell lines for the expression of a gene of interest in a host cell, the method comprising: transfecting a host cell with the expression vector; and, culturing the transfected host cell. According to an embodiment, the cell lines are produced in accordance with the method of producing the cell lines.

In respect of the features described above in relation to one or more aspects or embodiments of the invention, it should be understood that any two or more of the features may be combined in any appropriate combination. The polynucleotide has been found to be advantageous over prior art vectors in several ways. Stable cell lines using expression vectors comprising the polynucleotide sequence have been obtained within a very short period of time as compared to the prior art vectors which do not include the polynucleotide sequence. Furthermore, the polynucleotide also enables the gene to be insulated from repressive effects of neighbouring chromatin or regulatory elements. Surprisingly, they also increase the overall expression of the transgene the polynucleotide improves the probability of high expressing cell line and increase the stability and viability of expressed product.

The examples given below in a non-limiting manner will make it possible to better understand the invention:

EXAMPLE 1

Pbgmesv: The vector pBGMESV (FIG. 1) contains the Chicken lysozyme Matrix attachment region upstream of PEF-1 alpha promoter, PEF-1 alpha promoter is operably linked to multiple cloning site followed by BGH polyadenylation sequence. Gene for HSP 27 is linked to hCMV promoter. The gene for DHFR selection marker linked to IRES wherein the thymidine kinase polyadenylation sequence is linked to 5' end of DHFR gene. The gene for HSP27 and DHFR are arranged in a manner which allows the transcription of a single mRNA containing the sequence of HSP27 and DHFR. The mRNA also contains sequence for the internal ribosome entry site which allows the initiation of the translation of the DHFR protein. The complete sequence of gene coding for hCMV promoter is linked to HSP 27 gene which is connected to IRES linked DHFR gene having thymidine kinase Polyadenylation sequence at 5' end. The thymidine kinase polyadenylation sequence carries out the termination of transcription. The vector also contains bacterial selection marker i.e. gene for Ampicillin resistance for selection of transformants in bacteria more specifically in *E.coli*. The vector also contains gene acting as origin of replication in bacteria. The hCMV promoter is operably linked to gene for HSP. Gene for DHFR is operably linked to EMCV IRES at 3' end and TK polyadenylation sequence at 5' end. The gene of interest is cloned in the multiple cloning sites. The size of pBGMESV is 9516 bp.

EXAMPLE 2

Comparison of expression efficiencies of pBUD-EPO and pBGMESV-EPO by transient transfection. Host cells i.e suspension adapted CHO-DHFR⁻ (created from adaptation of CHO-DHFR⁻ adherant.cell lines provided by NCCS, Pune, India) were maintained in complete growth medium (CHO EXCELL-DHFR medium (Invitrogen) supplemented with 100 µM Hypoxanthine, 16 µM Thymidine and 6 mM glutamine) at a temperature of 37° C. and in an atmosphere of 5% $CO_2$. Cells were seeded at the density of $0.5 \times 10^6$/ml in a 6-well plate, 24 hours prior to electroporation Transfection was carried out using Neon Eletroporator (Invitrogen). Both the vectors were transfected into CHO DHFR⁻ cells and expression level was studied. 3 µg of vector DNA was added to 100 µl media containing $1 \times 10^6$ cells in electroporation cuvette and electroporated at 1600 Volts with 3 pulses expecting an electroporation time of around 10 millisec. Following electroporation, 100 µl volume of cells was transferred to 6-well plate comprising 2 ml medium. The plate was then gently swirled to ensure proper mixing and incubated for 48 hours at 37° C. in 5% $CO_2$. The spent media was collected from the 6 well-plate at 48 hours. The expression of EPO was analyzed by EPO Immunoassay kit (R & D Systems).

EXAMPLE 3

Analysis of expression yields achieved using EPO Immunoassay kit (R&D Systems). Supernatants from all wells of 6 well plate containing transformed cells growing for 48 hours was collected and diluted appropriately with specimen diluent. Standard dilutions were prepared between the ranges of 0-200 mIU. 100 µl of assay diluent was added to each well of micro titer plate. 100 µl of diluted samples were added to the wells. EPO standards provided in the kit were added to standard lane as follows: 200 mIU/ml, 100 mIU/ml, 50 mIU/ml, 20 mIU/ml, 5 mIU/ml, 2.5 mIU/ml, and 0 mIU/ml. Samples were incubated for 2 hours to allow antigen-antibody binding to take place. The plates were tapped to remove the unbound antibody. 100 µl of HRP-Conjugated antibody (Polyclonal rabbit antibody against recombinant human-EPO) was added to all the micro titer wells and further incubated at room temperature for 2 hours followed by washing (three times) using 300 µl of 1× wash buffer provided in kit. 100 µl of each colour reagent A and B were added to each well and incubated in dark for approximately 20-25 minutes. The reaction was stopped by addition of 100 µl of 2N sulfuric acid. Absorbance was measured in ELISA reader (Fluostar Galaxy) at 450 nm. Standard graph of O.D (450 nm) Vs. Concentration (ng/ml) was plotted and values of unknown samples were derived from the equation. FIG. 2 depicts representative data for yield achieved for transient transfection of CHO DHFR⁻ cells with pBGMESV-EPO and pBUD-EPO expression vectors. The highest expression was obtained with pBGMESV-EPO was 16 µg/ml/day whereas pBUD-EPO showed expression level of 745 ng/ml/day.

EXAMPLE 4

Stable transfection of suspension adapted CHO DHFR⁻ cells with pBGMESV-EPO construct. Suspension adapted CHO DHFR⁻ (created from adaptation of CHO-DHFR⁻ adherent cell lines provided by NCCS, Pune, India) cells were cultured in Hypoxanthine-Thymidine (HT) lacking EXCELL-DHFR medium (Invitrogen) comprising of 6 mM glutamine. Media change was given to the cells 24 hours prior to electroporation. 3 µg DNA was added to 100 µl media containing $1 \times 10^6$ cells in electroporation cuvette and electroporation was carried out at 1600 Volts with 3 pulses of an electroporation time of around 10 msec. Following electroporation, 100 µl medium containing $1 \times 10^6$ cells was transferred to 6-well plate comprising 2 ml medium. The plate was incubated for 48 hours at 37° C. in 5% $CO_2$ Cell count was performed using Trypan blue dye exclusion method, 48 hours post electroporation. Based on the cell count, the medium was diluted to perform single cell cloning. 20 nM MTX pressure was maintained in the diluted culture. The plates were observed on a standard inverted microscope for confirming the single cell cloning. Transfectants were further incubated for 25 days at 37° C. in 5% $CO_2$ for colony formation. Individual colonies were analyzed for EPO production using EPO Immunoassay kit (R&D Systems) as mentioned in example 3.

EXAMPLE 5

Clone Selection and gene amplification. Clones showing High expression were selected and were subjected to methotrexate (MTX)—based gene amplification process. 20 nM MTX was added to the selection media (CHO Excell DHFR Medium) lacking Hypoxanthine-Thymidine and supplemented with 6 mM glutamine. Media was changed after every three days. The cells were grown in same concentration of MTX for about 15-20 days. Populations that reached normal growth at chosen level of drug were used for next round of selection. Expression of each clone was analyzed after every stage of increasing concentration of MTX. All the selected clones were subjected to sequential increasing MTX concentrations of 20 nM, 100 nM, 200 nM, 400 nM and finally, 2 µM MTX. The results were expressed as total amount of EPO protein secreted/$10^6$ cells/ml. High expressing clones were expanded and frozen down as master cell bank for commercial production of EPO.

EXAMPLE 6

Evaluation of nutritional stress of cell lines (comparison of CHO-S Relipofection HSP 27 and Plain CHO-S HSP 27). A comparative study between a mammalian cell clone pBGMESV vector and a vector without HSP gene and MAR gene was conducted to analyse the impact of HSP gene in presence of MAR gene in the vector. The Culture conditions were maintained for both the culture flasks similar to described in example 4. Experiment was conducted in batch fermentation mode, to impart nutritional stress on the culture flasks. Mammalian cells of pBGMESV vector and a vector without HSP and MAR genes were seeded at 0 3 million cells/ml density in separate 125 ml shake flasks containing 10 ml of complete, chemically defined medium. After seeding, 0.2 ml of sample was taken out for performing cell count and cell viability with the help of Hemocytometer and Trypan blue dye exclusion method. Results were noted in the observation tables as Day zero readings and the culture flasks were incubated on a shaker maintained at 130 rpm in the CO2 incubator maintained at 37° C. temperature and 8% CO2.

Post day-2, cell count and cell viability were analysed after every 24 hrs, till the culture viability reached 0% and readings were noted in the observation tables. Glucose concentration in both the culture flasks was analysed periodically with the help of glucometer. The cell count and cell viability of the mammalian cells in pBGMESV vector and a vector without HSP and MAR are depicted in FIGS. 4a and 4b. Based on the above experiment, culture with HSP and MAR sustained viability for 24 hrs more than the culture without HSP. It was observed that increase in viable cell density of culture with HSP and MAR was observed till day-5, while there was no significant increase in viable cell density of non HSP culture. Lack of glucose as seen in FIGS. 4a and 4b, post day-5 suggested that the culture is deprived of nutrition, thus it can be inferred that the culture is under nutritional stress pBGMESV vector with HSP and MAR could sustain viability for 24 hrs more than the culture without MAR and HSP due to their ability to combat nutritional stress. Similarly increase in viable cell density was observed in culture with HSP and MAR while with similar culture conditions non HSP and MAR cells failed to divide post lack of glucose. Hence it can be concluded that HSP along with MAR sequence in pBGMESV vector makes the culture stress resistant.

During heat shock, both constitutive and stress-inducible HSPs bind to and inhibit irreversible aggregation of denatured protein and facilitate their refolding once normal cellular conditions are re-established. The dual role of HSP's in both normal and stressed cells, evidently requires the existence of complex regulatory processes which ensure that the correct expression pattern is produced. MAR helps to generate and maintain an open chromatin domain that is favourable to transcription and may also facilitate the integration of several copies of the transgene. Thus, incorporating HSP in presence of MAR gene in a pBGMESV vector leads to an elongated fermentation cycles at industrial scale resulting to higher production of recombinant proteins.

From the foregoing, it will be observed that numerous modifications and variations can be effectuated without departing from the true spirit and scope of the novel concepts of the present invention. It is to be understood that no limitation with respect to the specific embodiments illustrated is intended or should be inferred.

What we claim is:

1. An expression vector for expressing a recombinant protein in a mammalian cell, the vector comprising:
    in the following operative order, a first promoter, a first sequence coding for a stress resistance protein, an internal ribosome entry site (IRES), and a second sequence coding for a selection marker, wherein the first and second sequences are arranged to allow transcription of a single mRNA from the first promoter that encodes the stress resistance protein and the selection marker;
    a matrix attachment region (MAR); and
    a second promoter operably linked to multiple cloning site for inserting a third sequence coding for the recombinant protein.

2. The expression vector of claim 1, wherein the expression vector comprises the sequence of SEQ ID NO:1.

3. The expression vector of claim 1, wherein the first promoter is a hCMV promoter or a HSP promoter.

4. The expression vector of claim 1, wherein the second promoter is a PEF 1 alpha promoter.

5. The expression vector of claim 1, wherein the IRES a Picornavirus IRES, an Aphthovirus IRES, a Hepatitis A IRES, a Hepatitis C IRES, a Pestivirus IRES, a Cripavirus IRES, or a Kaposi sarcoma associated herpesvirus IRES.

6. The expression vector of claim 1, wherein the stress resistance protein is a HSP 70 protein, a HSP 90 protein, or a HSP27 protein.

7. The expression vector of claim 1, wherein the stress resistance protein is a HSP27 protein.

8. The expression vector of claim 1, wherein the selection marker is a glutamine synthatase, a dihydrofolate reductase, an antibiotic resistance, or an auxotrophic marker.

9. The expression vector of claim 1, wherein the selection marker is a dihydrofolate reductase.

10. The expression vector of claim 1, wherein the MAR is a chicken lysozyme MAR element.

* * * * *

SEQUENCE LISTING

<160> NUMBER OF SEQ ID NOS: 1

<210> SEQ ID NO 1
<211> LENGTH: 9516
<212> TYPE: DNA
<213> ORGANISM: Escherichia coli

<400> SEQUENCE: 1

```
gcgcgcgttg acattgatta ttgactagtt attaatagta atcaattacg gggtcattag        60
ttcatagccc atatatggag ttccgcgtta cataacttac ggtaaatggc ccgcctggct       120
gaccgcccaa cgaccccgc ccattgacgt caataatgac gtatgttccc atagtaacgc       180
caatagggac tttccattga cgtcaatggg tggactattt acggtaaact gcccacttgg       240
cagtacatca agtgtatcat atgccaagta cgccccctat tgacgtcaat gacggtaaat       300
ggcccgcctg gcattatgcc cagtacatga ccttatggga ctttcctact tggcagtaca       360
tctacgtatt agtcatcgct attaccatgg tgatgcggtt ttggcagtac atcaatgggc       420
gtggatagcg gtttgactca cggggatttc caagtctcca ccccattgac gtcaatggga       480
gtttgttttg gcaccaaaat caacgggact ttccaaaatg tcgtaacaac tccgccccat       540
tgacgcaaat gggcggtagg cgtgtacggt gggaggtcta tataagcaga gctcgtttag       600
```

```
tgaaccgtca gatcgcctgg agacgccatc cacgctgttt tgacctccat agaagacacc    660
gggaccgatc cagcctccgg actctagagg atccaaccct tgccgccacc atgaccgagc    720
gccgcgtgcc cttctcgctg ctgcggagcc cgagctggga accattccgg gactggtacc    780
ctgcacacag ccgcctcttc gatcaagctt tcggggtgcc ccggttgccc gatgagtggt    840
cgcagtggtt cagcgccgct gggtggcccg gatacgtgcg cccgctgccc gccgcgaccg    900
ccgagggccc cgcggcggtg accctggccg caccagcctt cagccgagcg ctcaaccgac    960
agctcagcag cggggtctcg gagatccgac agacggctga tcgctggcgc gtgtccctgg   1020
acgtcaacca cttcgctggc gaggagctca cagtgaagac caaggaaggc gtggtggaga   1080
tcactggcaa gcacgaagaa aggcaggacg aacatggcta catctctcgg tgcttcaccc   1140
ggaaatacac gctccctcca ggtgtggacc ccaccctagt gtcctcttcc ctatcccctg   1200
agggcacact taccgtggag gctccgttgc ccaaagcagt cacgcagtcg gcggagatca   1260
ccattccggt tactttcgag gcccgcgccc aaattggggg cccagaagct gggaaagtct   1320
gaaagggttg gatccctacc ggtgctgcgg ccgcgcagtt aacgccgccc ctctcccctcc   1380 cccccccta acgttactgg ccgaagccgc ttggaataag gccggtgtgc gtttgtctat   1440
atgttatttt ccaccatatt gccgtctttt ggcaatgtga gggcccggaa acctggccct   1500
gtcttcttga cgagcattcc taggggtctt tcccctctcg ccaaaggaat gcaaggtctg   1560
ttgaatgtcg tgaaggaagc agttcctctg gaagcttctt gaagacaaac aacgtctgta   1620
gcgacccttt gcaggcagcg gaaccccca cctggcgaca ggtgcctctg cggccaaaag   1680
ccacgtgtat aagatacacc tgcaaaggcg gcacaacccc agtgccacgt tgtgagttgg   1740
atagttgtgg aaagagtcaa atggctctcc tcaagcgtat tcaacaaggg gctgaaggat   1800
gcccagaagg tacccattg tatgggatct gatctggggc ctcggtacac atgctttaca   1860
tgtgtttagt cgaggttaaa aaacgtctaa ggccccccga accacggga cgtggttttc   1920 ctttgaaaaa cacgatgata atatggccac aagatctgcc accatggttc gaccattgaa   1980
ctgcatcgtc gccgtgtccc aaaatatggg gattggcaag aacggagacc taccctggcc   2040
tccgctcagg aacgagttca agtacttcca aagaatgacc acaacctctt cagtggaagg   2100
taaacagaat ctggtgatta tgggtaggaa aacctggttc tccattcctg agaagaatcg   2160
acctttaaag gacagaatta atatagttct cagtagagaa ctcaaagaac caccacgagg   2220
agctcatttt cttgccaaaa gtttggatga tgccttaaga cttattgaac aaccggaatt   2280
ggcaagtaaa gtagacatgg tttggatagt cggaggcagt tctgtttacc aggaagccat   2340
gaatcaacca ggccacctca gactctttgt gacaaggatc atgcaggaat ttgaaagtga   2400
cacgtttttc ccagaaattg atttggggaa atataaactt ctcccagaat acccaggcgt   2460
cctctctgag gtccaggagg aaaaaggcat caagtataag tttgaagtct acgagaagaa   2520
agactaaaac cggttagtaa tgagtttaaa cgggggaggc taactgaaac acggaaggag   2580
acaataccgg aaggaacccg cgctatgacg gcaataaaaa gacagaataa aacgcacggg   2640
tgttgggtcg tttgttcata acgcggggt tcggtcccag ggctggcact ctgtcgatac   2700
cccaccgaga ccccattggg gccaatacgc ccgcgtttct tccttttccc caccccaccc   2760
cccaagttcg ggtgaaggcc cagggctcgc agccaacgtc ggggcggcag gccctgccat   2820
taccgtcgac ctctagctag gcgcgcctta ccaatgctta atcagtgagg cacctatctc   2880
agcgatctgt ctatttcgtt catccatagt tgcctgactc cccgtcgtgt agataactac   2940
gatacgggag ggcttaccat ctggccccag tgctgcaatg ataccgcgag acccacgctc   3000
```

```
accggctcca gatttatcag caataaacca gccagccgga agggccgagc gcagaagtgg    3060
tcctgcaact ttatccgcct ccatccagtc tattaattgt tgccgggaag ctagagtaag    3120
tagttcgcca gttaatagtt tgcgcaacgt tgttgccatt gctacaggca tcgtggtgtc    3180
acgctcgtcg tttggtatgg cttcattcag ctccggttcc caacgatcaa ggcgagttac    3240
atgatccccc atgttgtgca aaaaagcggt tagctccttc ggtcctccga tcgttgtcag    3300
aagtaagttg gccgcagtgt tatcactcat ggttatggca gcactgcata attctcttac    3360
tgtcatgcca tccgtaagat gcttttctgt gactggtgag tactcaacca agtcattctg    3420
agaatagtgt atgcggcgac cgagttgctc ttgcccggcg tcaatacggg ataataccgc    3480
gccacatagc agaactttaa aagtgctcat cattggaaaa cgttcttcgg ggcgaaaact    3540
ctcaaggatc ttaccgctgt tgagatccag ttcgatgtaa cccactcgtg cacccaactg    3600
atcttcagca tcttttactt tcaccagcgt ttctgggtga gcaaaaacag gaaggcaaaa    3660
tgccgcaaaa aagggaataa gggcgacacg gaaatgttga atactcatac tcttccttt    3720 tcaatattat tgaagcattt atcagggtta ttgtctcatg agcggataca tatttgaatg    3780
tatttagaaa aataaacaaa taggggtgct agctctagaa acaatatat ttccaaatga    3840 aaaaaaaatc tgataaaaag ttgacttaaa aaagtatca ataaatgtat gcatttctca    3900
ctagccttaa actctgcatg aagtgtttga tgagcagatg aagacaacat catttctagt    3960
ttcagaaata ataacagcat caaaccgca gctgtaactc cactgagctc acgttaagtt    4020
ttgatgtgtg aatatctgac agaactgaca taatgagcac tgcaaggata tcagacaagt    4080
caaaatgaag acagacaaaa gtattttta atataaaaat ggtctttatt tcttcaatac    4140
aaggtaaact actattgcag tttaagacca acacaaaagt tggacagcaa attgcttaac    4200
agtctcctaa aggctgaaaa aaaggaaccc atgaaagcta aaagttatgc agtatttcaa    4260
gtataacatc taaaaatgat gaaacgatcc ctaaaggtag agattaacta agtacttctg    4320
ctgaaaatgt attaaaatcc gcagttgcta ggataccatc ttaccttgtt gagaaataca    4380
ggtctccggc aacgcaacat tcagcagact cttttggcctg ctggaatcag gaaactgctt    4440
actatataca catataaatc ctttggagtt gggcattctg agagacatcc atttcctgac    4500
attttgcagt gcaactctgc attccaactc agacaagctc ccatgctgta tttcaaagcc    4560
atttcttgaa tagtttaccc agacatcctt gtgcaaattg ggaatgagga atgcaatgg     4620 tacaggaaga caatacagcc ttatgtttag aaagtcagca gcgctggtaa tcttcataaa    4680
aatgtaactg ttttccaaat aggaatgtat ttcacttgta aaacacctgg tcctttttat    4740
attacttttt ttttttttta aggacacctg cactaatttg caatcacttg tatttataaa    4800
agcacacgca ctcctcattt tcttacattt gaagatcagc agaatgtctc tttcataatg    4860
taataatcat atgcacagtt taaaatattt tctattacaa aatacagtac acaagagggt    4920
gaggccaaag tctattactt gaatatattc caaagtgtca gcactggggg tgtaaaatta    4980
cattacatgg tatgaatagg cggaattctt ttacaactga aatgctcgat ttcattggga    5040
tcaaaggtaa gtactgttta ctatcttcaa gagacttcaa tcaagtcggt gtatttccaa    5100
agaagcttaa aagattgaag cacagacaca ggccacacca gagcctacac ctgctgcaat    5160
aagtggtgct atagaaagga ttcaggaact aacaagtgca taatttacaa atagagatgc    5220
tttatcatac tttgcccaac atgggaaaaa agacatccca tgagaatatc caactgagga    5280
acttctctgt tcatagtaa ctcatctact actgctaaga tggtttgaaa agtacccagc    5340
aggtgagata tgttcgggag gtggctgtgt ggcagcgtgt cccaacacga cacaaagcac    5400
```

```
cccacccata tctgcaatgc tcactgcaag gcagtgccgt aaacagctgc aacaggcatc    5460
acttctgcat aaatgctgtg actcgttagc atgctgcaac tgtgtttaaa acctatgcac    5520
tccgttacca aaataattta agtcccaaat aaatccatgc agcttgcttc ctatgccaac    5580
atattttaga aagtattcat tcttctttaa gaatatgcac gtggatctac acttcctggg    5640
atctgaagcg atttatacct cagttgcaga agcagtttag tgtcctggat ctgggaaggc    5700
agcagcaaac gtgcccgttt tacatttgaa cccatgtgac aacccgcctt actgagcatc    5760
gctctaggaa atttaaggct gtatccttac aacacaagaa ccaacgacag actgcatata    5820
aaattctata aataaaaata ggagtgaagt ctgtttgacc tgtacacaca gagcatagag    5880
ataaaaaaaa aaggaaatca ggaattacgt atttctataa atgccatata ttttactag    5940 aaacacagat gacaagtata tacaacatgt aaatccgaag ttatcaacat gttaactagg    6000
aaacatttta caagcatttg ggtatgcaac tagatcatca ggtaaaaaat cccattagaa    6060
aaatctaagc ctcgccagtt tcaaggaaa aaaaccagag aacgctcact acttcaaagg    6120 aaaaaaata aagcatcaag ctggcctaaa cttaataagg tatctcatgt aacaacagct    6180
atccaagctt tcaagccaca ctataaataa aaacctcaag ttccgatcaa cgttttccat    6240
aatgcaatca gaaccaaagg cattggcaca gaaagcaaaa agggaatgaa agaaaagggc    6300
tgtacagttt ccaaaaggtt cttcttttga agaaatgttt ctgacctgtc aaaacataca    6360
gtccagtaga aattttacta agaaaaaaga acaccttact taaaaaaaaa aaacaacaaa    6420
aaaaacaggc aaaaaaacct ctcctgtcac tgagctgcca ccacccaacc accacctgct    6480 gtgggcttg tctcccaaga caaggacac acagccttat ccaatattca acattactta    6540
taaaaacgct gatcagaaga aataccaagt atttcctcag agactgttat atcctttcat    6600
cggcaacaag agatgaaata caacagagtg aatatcaaag aaggcggcag gagccaccgt    6660
ggcaccatca ccgggcagtg cagtgcccaa ctgccgtttt ctgagcacgc ataggaagcc    6720
gtcagtcaca tgtaataaac caaaacctgg tacagttata ttatggatcc gctagcttcg    6780
tgaggctccg gtgcccgtca gtgggcagag cgcacatcgc ccacagtccc cgagaagttg    6840
ggggggaggg tcggcaattg aaccggtgcc tagagaaggt ggcgcggggt aaactgggaa    6900
agtgatgtcg tgtactggct ccgcctttt cccgaggtg ggggagaacc gtatataagt    6960
gcagtagtcg ccgtgaacgt tcttttcgc aacgggttg ccgccagaac acaggtaagt    7020
gccgtgtgtg gttcccgcgg gcctggcctc tttacgggtt atggcccttg cgtgccttga    7080
attacttcca cctggctcca gtacgtgatt cttgatcccg agctggagcc agggcgggc    7140 cttgcgcttt aggagcccct tcgcctcgtg cttgagttga ggcctggcct gggcgctggg    7200
gccgccgcgt gcgaatctgg tggcaccttc gcgcctgtct cgctgctttc gataagtctc    7260
tagccattta aaattttga tgacctgctg cgacgctttt ttttctggcaa gatagtcttg    7320 taaatgcggg ccaggatctg cacactggta tttcggtttt tgggcccgcg gccggcgacg    7380
gggcccgtgc gtcccagcgc acatgttcgg cgaggcgggg cctgcgagcg cggccaccga    7440
gaatcggacg ggggtagtct caagctggcc ggcctgctct ggtgcctggc ctcgcgccgc    7500
cgtgtatcgc cccgccctgg gcggcaaggc tggcccggtc ggcaccagtt gcgtgagcgg    7560
aaagatggcc gcttcccggc cctgctccag ggggctcaaa atggaggacg cggcgctcgg    7620
gagagcgggc gggtgagtca cccacacaaa ggaaaagggc ctttccgtcc tcagccgtcg    7680
cttcatgtga ctccacggag taccgggcgc cgtccaggca cctcgattag ttctggagct    7740
tttggagtac gtcgtccttta ggttggggg agggggtttta tgcgatggag tttcccccaca    7800
```

-continued

```
ctgagtgggt ggagactgaa gttaggccag cttggcactt gatgtaattc tcgttggaat    7860
ttgcccttt  tgagtttgga tcttggttca ttctcaagcc tcagacagtg gttcaaagtt    7920
tttttcttcc atttcaggtg tcgtgaacac gtggtcgcgg ccgcttcgaa ggtaccagca    7980
cagtggactc gagatcgatc ccgggcctgc aggcgtacga gatctggccg gctgggcccg    8040
tttcgaaggt aagcctatcc ctaaccctct cctcggtctc gattctacgc gtaccggtca    8100
tcatcaccat caccattgag tttaaacccg ctgatcagcc tcgactgtgc cttctagttg    8160
ccagccatct gttgtttgcc cctcccccgt gccttccttg accctggaag gtgccactcc    8220
cactgtcctt tcctaataaa atgaggaaat tgcatcgcat tgtctgagta ggtgtcattc    8280
tattctgggg ggtggggtgg ggcaggacag caaggggag gattgggaag acaatagcag     8340
gcatgctggg gatgcggtgg gctctatggc ttctgaggcg gaaagaacca gtggcggtaa    8400
tacggttatc cacagaatca ggggataacg caggaaagaa catgtgagca aaaggccagc    8460
aaaaggccag gaaccgtaaa aaggccgcgt tgctggcgtt tttccatagg ctccgccccc    8520
ctgacgagca tcacaaaaat cgacgctcaa gtcagaggtg gcgaaacccg acaggactat    8580
aaagatacca ggcgtttccc cctggaagct ccctcgtgcg ctctcctgtt ccgaccctgc    8640
cgcttaccgg atacctgtcc gcctttctcc cttcgggaag cgtggcgctt tctcatagct    8700
cacgctgtag gtatctcagt tcggtgtagg tcgttcgctc caagctgggc tgtgtgcacg    8760
aaccccccgt tcagcccgac cgctgcgcct tatccggtaa ctatcgtctt gagtccaacc    8820
cggtaagaca cgacttatcg ccactggcag cagccactgg taacaggatt agcagagcga    8880
ggtatgtagg cggtgctaca gagttcttga agtggtggcc taactacggc tacactagaa    8940
ggacagtatt tggtatctgc gctctgctga agccagttac cttcggaaaa agagttggta    9000
gctcttgatc cggcaaacaa accaccgctg gtagcggtgg tttttttgtt tgcaagcagc    9060
agattacgcg cagaaaaaaa ggatctcaag aagatccttt gatcttttct acggggtctg    9120
acgctcagtg gaacgaaaac tcacgttaag ggattttggt catgacatta acctataaaa    9180
ataggcgtat cacgaggccc tttcgtctcg cgcgtttcgg tgatgacggt gaaaacctct    9240
gacacatgca gctcccggag acggtcacag cttgtctgta agcggatgcc gggagcagac    9300
aagcccgtca gggcgcgtca gcgggtgttg gcgggtgtcg gggctggctt aactatgcgg    9360
catcagagca gattgtactg agagtgcacc atatatgcgg tgtgaaatac cgcacagatg    9420
cgtaaggaga aataccgca tcaggcgcca ttcgccattc aggctgcgca actgttggga    9480
agggcgatcg gtgcgggcct cttcgctatt acgcca                              9516
```